(12) United States Patent
Yasutake et al.

(10) Patent No.: US 6,499,340 B1
(45) Date of Patent: Dec. 31, 2002

(54) SCANNING PROBE MICROSCOPE AND METHOD OF MEASURING GEOMETRY OF SAMPLE SURFACE WITH SCANNING PROBE MICROSCOPE

(75) Inventors: Masatoshi Yasutake, Chiba (JP); Akira Inoue, Chiba (JP); Akihiko Homma, Chiba (JP); Ryuichi Matsuzaki, Chiba (JP); Gerd K. Binnig, Wollerau (CH); Walter Haeberle, Waedenswil (CH)

(73) Assignees: Seiko Instruments Inc. (JP); International Business Machines Corporation

( * ) Notice: Subject to any disclaimer, the term of this patent is extended or adjusted under 35 U.S.C. 154(b) by 0 days.

(21) Appl. No.: 09/252,397

(22) Filed: Feb. 18, 1999

(30) Foreign Application Priority Data

Feb. 19, 1998 (JP) .......................... 10-037352
Jan. 28, 1999 (JP) .......................... 11-020578

(51) Int. Cl.⁷ ............................. H01J 37/26; G01B 5/28
(52) U.S. Cl. ........................................ 73/105; 250/306
(58) Field of Search ........................... 73/105; 250/306, 250/307

(56) References Cited

U.S. PATENT DOCUMENTS

| | | | | |
|---|---|---|---|---|
| RE33,387 E | * | 10/1990 | Binnig ..................... | 250/306 |
| 5,415,027 A | * | 5/1995 | Elings et al. .............. | 73/105 |
| 5,503,010 A | * | 4/1996 | Yamanaka ................. | 73/105 |
| 5,624,845 A | * | 4/1997 | Wickramasinghe et al. | 250/306 |
| 5,666,190 A | * | 9/1997 | Quate et al. .............. | 355/71 |
| 5,729,015 A | * | 3/1998 | Tong ....................... | 73/105 |
| 5,804,708 A | * | 9/1998 | Yamanaka et al. ......... | 73/105 |
| 5,939,715 A | * | 8/1999 | Kitamura et al. .......... | 250/306 |
| RE36,488 E | * | 1/2000 | Elings et al. .............. | 73/105 |
| 6,172,506 B1 | * | 1/2001 | Adderton et al. .......... | 73/105 |

FOREIGN PATENT DOCUMENTS

JP          07140153 A  *  6/1995

OTHER PUBLICATIONS

Maivald, P et al. "Using force modulation to image surface elasticities with the atomic force microscope", Nanotechnology vol. 2 (1991), pp. 103–106.*

* cited by examiner

Primary Examiner—Hezron Williams
Assistant Examiner—Michael Cygan
(74) Attorney, Agent, or Firm—Adams & Wilks (57) ABSTRACT

A measuring method and apparatus of a scanning probe microscope which is easy to initially set caused by exchanging a cantilever. A cantilever is effected of Z rough movement while forcibly vibrating a sample. When a contact pressure of the cantilever against the sample becomes a predetermined magnitude, the Z rough movement is ended. The forcible vibrational frequency may be a new resonant frequency caused by contacting the cantilever with the sample, or a shift resonant frequency. Then, XY scanning is effected to measure while putting the cantilever into light contact with a sample surface. It is possible to use, as an apparatus to forcibly vibrate the cantilever, a multi-layer piezoelectric element that responds to an output signal from an oscillator for outputting a signal at a predetermined frequency.

14 Claims, 6 Drawing Sheets

SCANNING PROBE MICROSCOPE AND METHOD OF MEASURING GEOMETRY OF SAMPLE SURFACE WITH SCANNING PROBE MICROSCOPE

BACKGROUND OF THE INVENTION

1. Field of the Invention

This invention relates to a method of measuring a surface geometry of a sample using a scanning probe microscope and an apparatus therefor, and more particularly to a measuring method with and apparatus of a scanning probe microscope adapted to measure a surface geometry of a sample by vibrating the sample.

2. Background Information

There is known a measuring method, as a conventional measuring method for measuring a surface geometry of a sample by using a scanning probe microscope, wherein a cantilever is resonantly vibrated to lightly tap a sample surface and the cantilever is feedback-controlled in Z directional position (distance between the sample and the cantilever) by a servo system so as to bring constant the state of tapping, thereby obtaining geometry data on the sample surface. This method is generally referred to as a tapping mode.

According to this measuring method, there possesses a merit that the Q value of cantilever resonant frequency, at a resonant frequency f0, becomes approximately 100–300 and large amplitude of vibration is obtainable even if the cantilever is vibrated by an oscillator with small amplitude output.

However, in the above conventional measuring method the resonant frequency f0 and the resonant frequency Q value vary for each cantilever. There has been a problem that, if the cantilever is exchanged, time is required for adjustment until starting a sample surface measurement and further the adjustment necessitates experience. In particular, if the Q value changes, the amplitude of cantilever vibration varies. Accordingly, there has been a problem that there is difficulty in causing the cantilever to perform Z rough movement to a position at which a needle tip of the cantilever lightly tap the sample surface. Also, there has been a problem that, although the needle tip urging pressure against the sample surface varies between a shallow Z rough movement case and a deep case, the change of urging pressure causes the sample surface detection data to vary thus resulting in variation in observation image on the same sample.

It is an object of the present invention to eliminate the above-stated problems in the conventional art and provide a measuring method with and apparatus of a scanning probe microscope which, even if the cantilever is exchanged, can easily initially set constant at all times the pressure that a needle tip of a cantilever taps a sample surface.

Also, it is another object to provide a measuring method with and apparatus of a scanning probe microscope by which, even if the cantilever is exchanged, variation-free and stable detection for the sample surface data can be obtained.

SUMMARY OF THE INVENTION

In order to achieve the above-described object, the present invention is a scanning probe microscope measuring method of measuring a geometry of a surface of a sample by contacting a cantilever with the surface of the sample, the scanning probe microscope measuring method characterized in that: the geometry of the sample surface is measured while putting the cantilever in light contact with the sample surface in a state that the sample is being vibrated at a frequency that is substantially free of affection of resonant frequencies inherent to the cantilever and the sample.

The vibrational frequency of the sample may be a new resonant frequency of the cantilever shifted by contacting the cantilever with the sample. Also, the vibrational frequency of the sample may be a resonant frequency caused by contacting the cantilever with the sample.

Also, according to the present invention, in a scanning probe microscope for measuring a surface of a sample, a structure is proposed that has: an oscillator which can output an electric signal at a frequency that is substantially free of affection of resonant frequencies inherent to the cantilever and the sample; a Z servo system for feedback-control on vertical movement of the cantilever; a vibrator for responding to an output signal of the oscillator and an output signal of the Z servo system, to vibrate the sample at a frequency that is substantially free of affection of resonant frequencies inherent to the cantilever and the sample; wherein the Z servo system holds equilibrium at a point where a contact pressure of the cantilever against the sample becomes a predetermined magnitude.

Furthermore, a scanning probe microscope according to the present invention may be, in the above structure, structured that the sample is vibrated at a resonant frequency caused by contacting the cantilever with the sample.

Also, according to the present invention, in a scanning probe microscope of measuring a geometry of a surface of a sample by contacting a cantilever with the surface of the sample, a structure is proposed that has: an oscillator which can output an electric signal of a new resonant frequency of the cantilever shifted by contacting the cantilever with the sample; a Z servo system for feedback-control on vertical movement of the cantilever; a vibrator for responding to an output signal of the oscillator and an output signal of the Z servo system, to vibrate the sample at the new resonant frequency; wherein the Z servo system holds equilibrium at a point where a contact pressure of the cantilever against the sample becomes a predetermined magnitude.

According to the method of the present invention, because the sample is vibrated by avoiding the resonant frequencies inherent to the cantilever and the sample, the measuring manner becomes simple as compared with the conventional measuring method in the tapping mode. Also, even if the cantilever is exchanged, it becomes possible to obtain constant observation images at all times.

In this case, it is possible to structure with using a resonant frequency newly caused when the cantilever comes into contact with the sample regardless of free vibration of the cantilever and the sample as single members. This can enhance sensitivity of measurement. Also, by vibrating at a new resonant frequency of the cantilever shifted due to contacting the cantilever with the sample, even if the cantilever possesses two or more resonant frequencies, measurement is possible provided that the resonant frequency caused by coupling between the sample and the probe needle lies at an intermediate between them.

In any case, because the sample is put in vibration and the cantilever is contacted with this, the vibrational amplitude of the cantilever tends to increase as the cantilever approaches the sample. Due to this, it is possible to increase detection sensitivity. In this manner, because of a detection method that the vibrational amplitude becomes maximum where the probe needle extremely approaches the sample in a manner different from the tapping mode, the S/N ratio of the detection signal improves where the probe needle extremely approaches the sample, thus stabilizing detection characteristics.

Also, according to the apparatus of the present invention, because the Z servo system holds equilibrium at a point where the contact pressure of the cantilever against the sample becomes a predetermined magnitude, the initial setting for measurement (Z rough movement) becomes easy to perform. The scanning probe microscope can be easily handled by one who is not skillful.

DETAILED DESCRIPTION OF THE PREFERRED EMBODIMENTS

The present invention will be explained in detail hereinunder with reference to the drawings.

Figure 1:
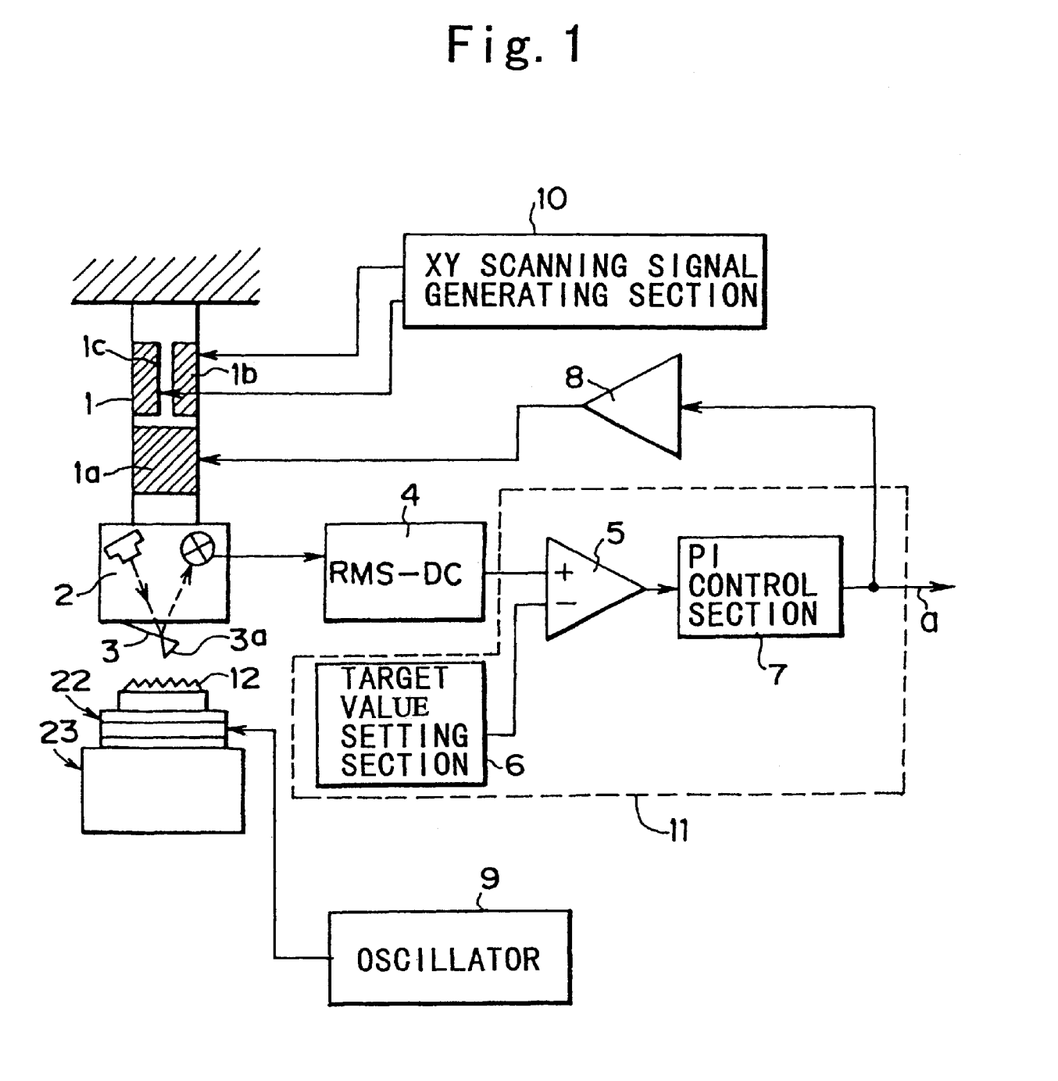
[FIG. 1] A block diagram of one embodiment of the present invention.

FIG. 1 is a block diagram showing a structure of one embodiment of the present invention. As shown in the figure, a piezoelectric scanner 1 fixed at its upper end has a lower end attached with a displacement detecting section 2 (hereinafter referred to as an optical lever detecting section) for a cantilever 3. An output signal of the optical lever detecting section 2 is inputted to an RMS-DC circuit (Root mean square-DC circuit, i.e., square mean smoothing circuit) 4, which is waveform-detected here and converted into a direct-current signal having a level dependent upon a displacement of the cantilever 3. An output signal of the RMS-DC circuit 4 is inputted to a comparator 5, and magnitude-compared with a target value set by a target value setting section 6. An output signal of the comparator 5 representative of a result of the magnitude comparison is inputted to a proportional integration (PI) control section 7.

An output signal of the proportional integration control section 7 is sent as an image signal a representative of a surface geometry of a sample 12 to a not-shown image display unit. Also, the output signal of the proportional integration control section 7 is sent to an amplifier 8. An output of the amplifier 8 is applied to a Z-direction drive electrode 1a of the piezoelectric scanner 1. Also, scanning signal outputs of an XY scanning signal generating section 10 are respectively applied to X, Y direction drive electrodes 1b, 1c. Incidentally, the comparator 5, the target value setting section 6, and the PI control section 7 constitute a Z servo system 11.

One denoted at reference character 9 is an oscillator that can output a voltage signal of 1–400 kHz. The output signal from the oscillator 9 is applied to a multi-layer piezoelectric element 22 acting as an oscillation applying device. The multi-layered piezoelectric element 22 is formed by layering in a same direction a plurality of piezoelectric plates same in polarity. The multi-layered piezoelectric element 22 is provided on a fixing table 23, and a sample 12 is placed on the multilayered piezoelectric element 22. If an output signal is applied from the oscillator 9 to the multi-layered piezoelectric element 22, the amounts of displacement of respective sheets are added together to give greater displacement. With the above structure, the sample 12 can be forcibly vibrated by the multi-layered piezoelectric element 22 at a same frequency as the frequency of the output signal of the oscillator 9.

Figure 2:
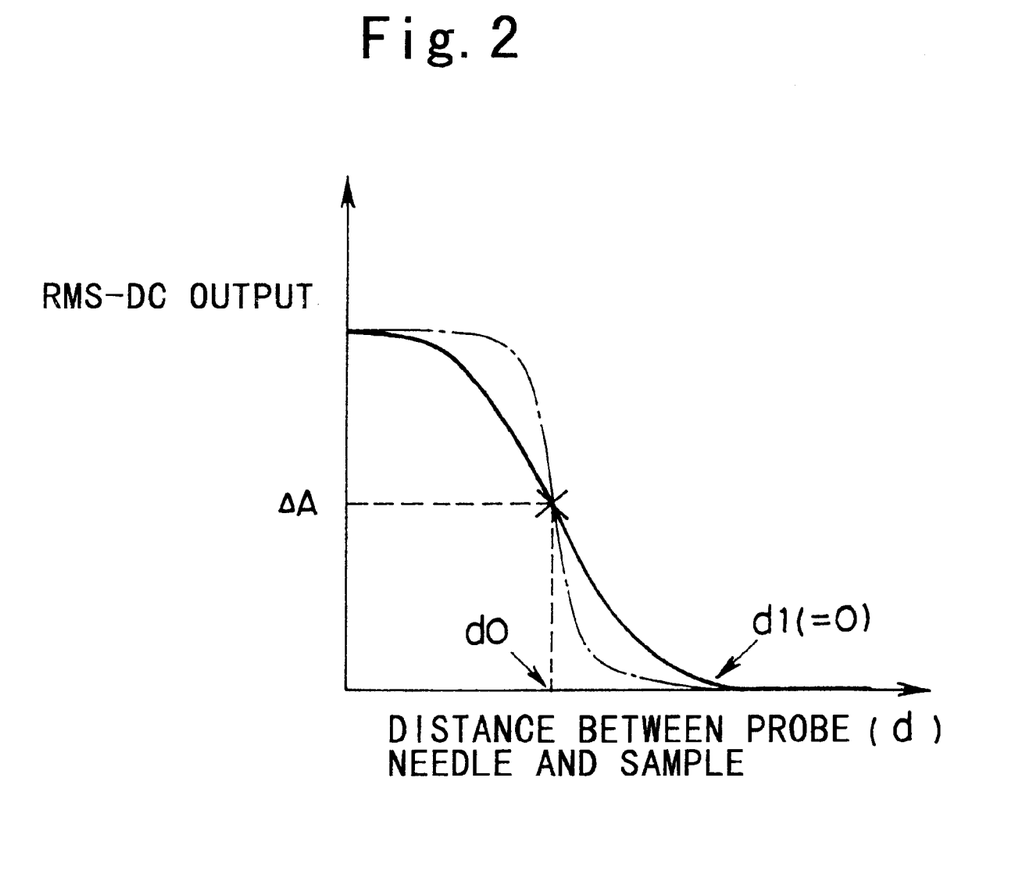
[FIG. 2] A diagram showing a relationship between a distance between a probe needle and a sample and an RMS-DC circuit output.

Then, the operation of the present embodiment will be explained in detail with reference to FIG. 1 and FIG. 2. Here, FIG. 2 represents a relationship between a distance d (horizontal axis) between a probe needle 3a provided at a tip of the cantilever 3 and a sample, and a value (vertical axis) of an output signal of the RMS-DC circuit. First, the oscillator 9 is operated in a state that the distance d between the probe needle 3a and the sample 12 is taken distant by a predetermined distance. An output signal of the oscillator 9 is applied to the multi-layered piezoelectric element 22 to thereby apply vibration in a vertical (Z) direction to the sample 12. At this time, the frequency of the oscillator 9 is adjusted such that the frequency of the sample 12 is substantially free from the affection of a resonant frequency inherent to each of the cantilever 3 and the sample 12. If in this manner the sample 12 is applied with vibration in the vertical (Z) direction by the multi-layered piezoelectric element 22 acting as a vibrator, the sample 12 is placed in a state of being forcibly vibrated with a predetermined constant amplitude. At this time, the probe needle 3a is largely distant from the sample 12, and the amplitude of the sample 12 is smaller than the distance d between the probe needle 3a and the sample. Accordingly, the probe needle 3a is free from contact with a sample surface, and the output signal of the RMS-DC circuit has a value 0.

Thereafter, a Z servo system 11 is actuated and a Z-direction drive electrode 1a of the piezoelectric scanner 1 is applied by a gradual increasing voltage. The optical lever detecting section 2 is lowered to decrease the distance d between the probe needle 3a and sample 12. Ultimately, the probe needle 3a comes into contact with the surface of the sample 12 in vibration. If this is done, the cantilever 3 undergoes a force from the sample 12 to thereby displace. This displacement is converted into an electric signal in the optical lever detecting section 2, and converted into a direct current by the RMS-DC circuit 4, being compared with a target value by a comparator 5.

In the present embodiment, because the target value is set at ΔA in FIG. 2, the probe needle 3a ceases Z rough movement at a position entering by (d1–d0) from the surface, at a time point of a maximum stroke of the forcible vibration of the sample 12. Thereafter a XY scanning signal generating section 10 is actuated to begin observation on the sample 12.

In the present embodiment, as stated before the sample 12 is forcibly vibrated by using the multi-layered piezoelectric element 22 due to the signal output of the oscillator 9. At this time, the frequency of the signal output of the oscillator 9 is made different from the resonant frequency of the cantilever 3. If, for example, the resonant frequency of the cantilever 3 is freso, the signal output frequency of the oscillator 9 is fosc and the operating region of the Z servo system is fservo, then freso>>fosc>fservo is given standing between these three frequencies.

Specifically, because the resonant frequency freso of the cantilever 3 is usually at 100–300 kHz, it is preferred that the oscillator 9 oscillation frequency fosc is at 1–20 kHz and the operating range fservo of the Z servo system is at approximately 1 kHz. Incidentally, the output signal amplitude of the oscillator 9, i.e., the forcible vibration amplitude of the sample 12, is determined at approximately 20–500 nm.

According to the present embodiment, the initial adjustment is ended at a time that the probe needle 3a comes into contact with the surface of the sample 12 at a predetermined contact pressure due to the Z rough movement. Thereafter, the surface of the sample 12 can be started to be observed while forcibly vibrating the sample 12. Accordingly, it is possible to initially set always constant the pressure that the cantilever 3 at its needle tip taps the surface of the sample 12 with ease even if the cantilever 3 is exchanged. Also, in the present embodiment, because no resonant frequency of the cantilever 3 is utilized, if the cantilever 3 is replaced, detection data on the sample surface becomes available stably at all times without variation. Because the sample being vibrated is contacted with the cantilever in this manner, the vibrational amplitude of the cantilever tends to increase as the cantilever approaches the sample. Due to this, it is possible to increase detection sensitivity. Also, because of a detection method that the vibrational amplitude reaches maximum where the probe needle extremely approaches the sample in a manner different from the tapping mode, there obtained is an improvement in detection signal S/N ratio where the probe needle extremely approaches the sample, thus stabilizing detection characteristics.

In this manner, in the above embodiment, there was shown the structure of forcibly vibrating the cantilever 3 by avoiding the resonant frequency of the cantilever 3. In this case, however, because the sensitivity is increased, a structure is feasible that the cantilever 3 is forcibly vibrated at a resonant frequency newly caused by contacting the cantilever 3 with the sample 12.

Figure 3:
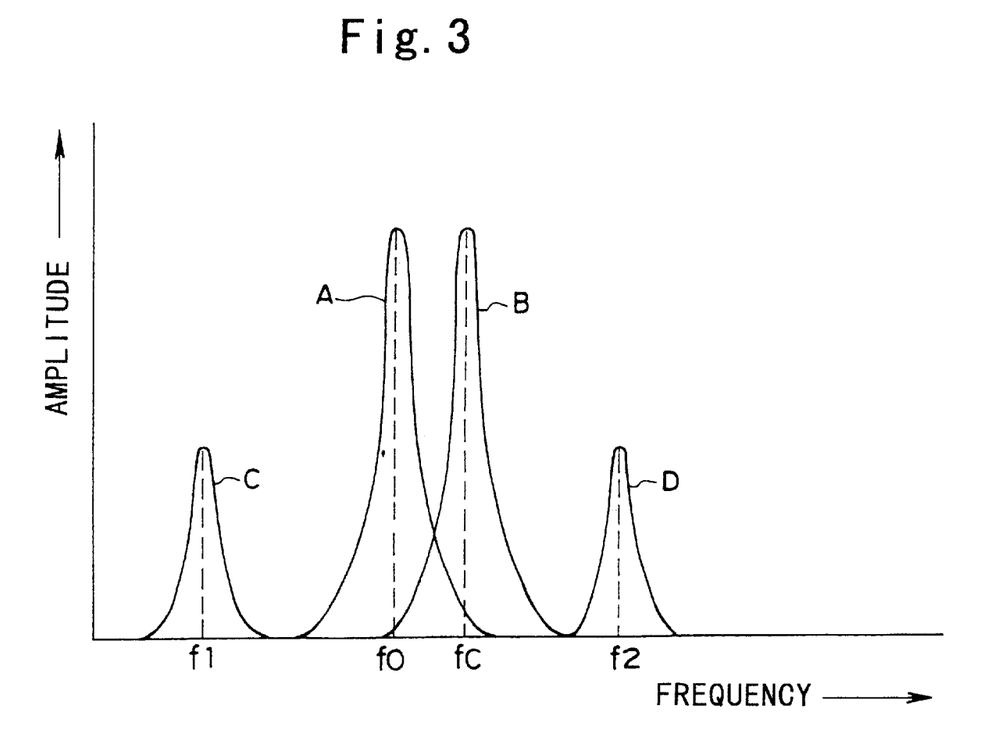
[FIG. 3] An explanatory diagram for explaining various vibrational characteristics of the cantilever.

FIG. 3 shows vibrational characteristics of the cantilever 3 in various states, wherein the frequency is taken on a horizontal axis while amplitude on a vertical axis. A curve shown at a reference character A is a vibrational characteristic obtained when the cantilever 3 is singly vibrated at a resonant frequency f0 of the cantilever 3. A curve shown at a reference character B represents a vibrational characteristic wherein the resonant frequency f0 of the cantilever 3 is shifted to fc by contacting the cantilever 3 with the sample 12 thereby somewhat shifting the vibrational characteristic A. Reference characters C, D represent new vibrational characteristics of the cantilever 3 by causing a new resonant frequencies f1, f2 upon contacting the cantilever 3 with the sample 12 in order for measurement.

In the case where the cantilever 3 is forcibly vibrated according to the present invention by an external force while avoiding its resonant frequency f0, it is possible to structure an apparatus with high sensitivity and performance by utilizing the new resonant frequencies f1, f2 as denoted by the reference characters C, D in FIG. 3.

That is, the oscillator 9 of FIG. 1 is made oscillatable within a range of approximately 1–400 KHz to match the oscillator 9 to the above frequency f1 or f2, whereby the cantilever 3 can be vibrated with higher efficiency thus structuring a measuring system with high sensitivity. Also the above frequency f1 or f2 is not largely varied if the cantilever 3 is exchanged. Therefore, it is possible to stably obtain detection data on the sample surface at all times without variation, as in the embodiment shown in FIG. 1.

Meanwhile, if such frequencies f1, f2 are used, the cantilever 3 is brought distant from the sample 12 to thereby cancel the resonant state at the frequency f1, f2. Accordingly, the amplitude of the cantilever 3 abruptly decreases due to the distant cantilever 3 from the sample 12. Therefore, the characteristic curve shown in FIG. 2 becomes a form, for example, as shown by a one-dot chain line. It becomes possible to detect with extreme accuracy as to contact or non-contact of the cantilever 3 with the sample 12.

Although in the above the embodiment was explained in the case of utilizing the frequency f1, f2, it is also possible to structure an apparatus having high sensitivity and performance by utilizing the shifted resonant frequency fc shown in FIG. 3.

That is, the oscillator 9 of FIG. 1 is made oscillatable within a range of approximately 1–400 KHz to match the output frequency of the oscillator 9 to the above frequency fc, whereby the sample 12 is vibrated at the frequency fc and the cantilever 3 is vibrated with higher efficiency when the cantilever 3 is contacted with the sample 12 thus structuring a measuring system with high sensitivity. Also because the above frequency fc is due to contact with the sample 12, it is not greatly varied if the cantilever is exchanged. Therefore, it is possible to stably obtain detection data on the sample surface at all times without variation, as in the embodiment shown in FIG. 1.

Meanwhile, if such a frequency fc is used, the cantilever 3 is brought distant from the sample 12 to thereby cancel the resonant state at the frequency fc. Accordingly, the amplitude of the cantilever 3 abruptly decreases due to the distant cantilever 3 from the sample 12, thus becoming a characteristic curve shown by a one-dot chain line in FIG. 2. It becomes possible to detect with extreme accuracy as to contact or non-contact of the cantilever 3 with the sample 12.

In this manner, if the cantilever 3 is vibrated at the new resonant frequency fc by avoiding the inherent resonant frequency f0 to the cantilever 3 as a single body, where the vibrational amplitude is smaller than the distance d between the probe needle 3a and the sample, there is no case that the probe needle 3a contacts with the sample surface and the RMS-DC circuit has an output signal value of 0.

Thereafter, the Z servo system 11 actuates to apply a gradually increasing voltage to the z-direction drive electrode 1a of the piezoelectric scanner 1. The optical lever detecting section 2 lowers to gradually decrease the distance d between the probe needle 3a and the sample 12. Then the probe needle 3a ultimately comes into contact with the vibrating surface of the sample 12. Thereupon the cantilever 3 undergoes a force from the sample 12 and displaces. This displacement is converted into an electric signal by the optical lever detecting section 2, converted into a direct current by the RMS-DC circuit 4, and compared with a target value by the comparator 5.

Because in the preset embodiment the target value is set at ΔA in FIG. 2, the cantilever 3 becomes resonantly vibrating due to the resonant frequency fc, at a position that the sample enters by (d1−d0) from its surface, at a time point of a maximum stroke of the forcible vibration due to the resonant frequency fc. The Z rough movement is ended. Thereafter, the XY scanning signal generating section 10 is actuated to begin observation on the sample 12.

In the present embodiment, the sample 12 is vibrated by a signal output with the frequency fc of the oscillator 9 as stated before. At this time, fc>fservo is given to stand, provided that the operating range of the Z servo system is fservo.

Specifically, because the new resonant frequency fc of the cantilever 3 is usually 100–300 kHz, the operating range fservo of the Z servo system is preferably determined at approximately 1 kHz. Incidentally, the vibrational amplitude of the sample 12 is determined as approximately 20–500 nm.

According to the present embodiment, the initial adjustment is ended at a time point that the probe needle 3a comes into contact with the surface of the sample 12 due to Z rough movement at a predetermined contact pressure. Thereafter, observation on the surface of the sample 12 can be commenced while vibrating the sample 12 at a new resonant frequency fc. Accordingly, it is possible to easily initially set the pressure to tap the surface of the sample 12 by a needle tip of the cantilever 3 at always constant even if the cantilever 3 is exchanged. Also, in the present embodiment, instead of the resonant frequency f0 for the single cantilever 3, the new resonant frequency fc is utilized that is to be somewhat shifted from the resonant frequency fc upon contacting the cantilever 3 with the sample 12. Accordingly, even if the cantilever 3 is exchanged, it becomes possible to stably obtain detection data on the sample surface at all times without variation.

Figure 6:
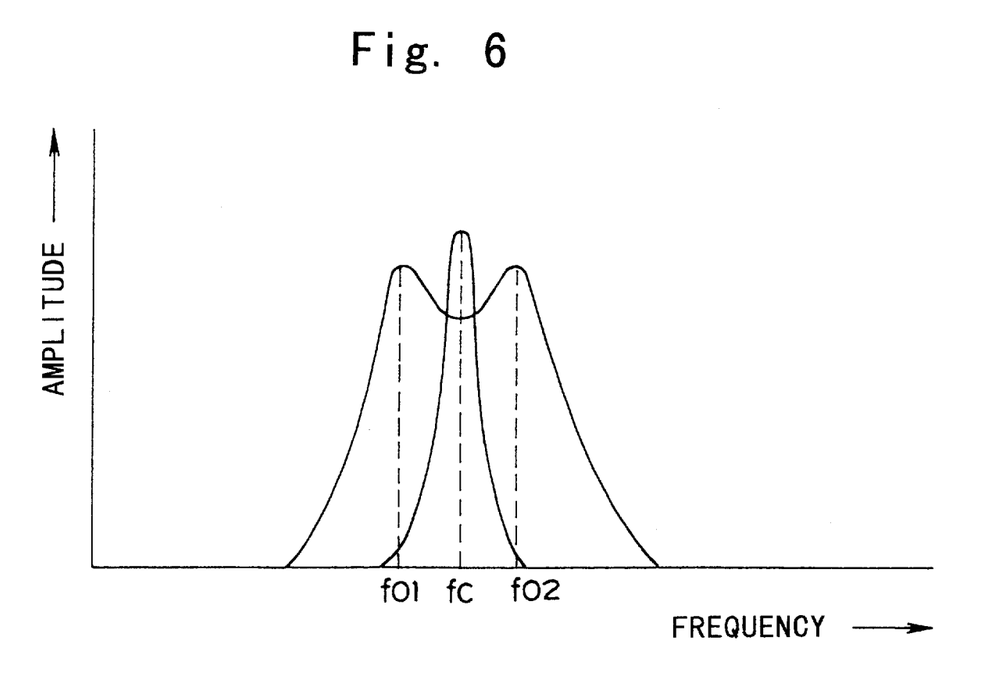
[FIG. 6] An explanatory diagram for explaining an advantage of the present invention in the case the cantilever possesses two resonant frequencies.

In the case where the resonant frequency fc is used as a vibrational frequency of the sample 12, even where the cantilever 3 has two resonant frequencies f01, f02 or three or more resonant frequencies, as shown in FIG. 6, there is an advantage that required measurements are possible provided that the resonant frequency fc caused by coupling between the sample 12 and the probe needle 3a lies intermediate between them.

Figure 4:
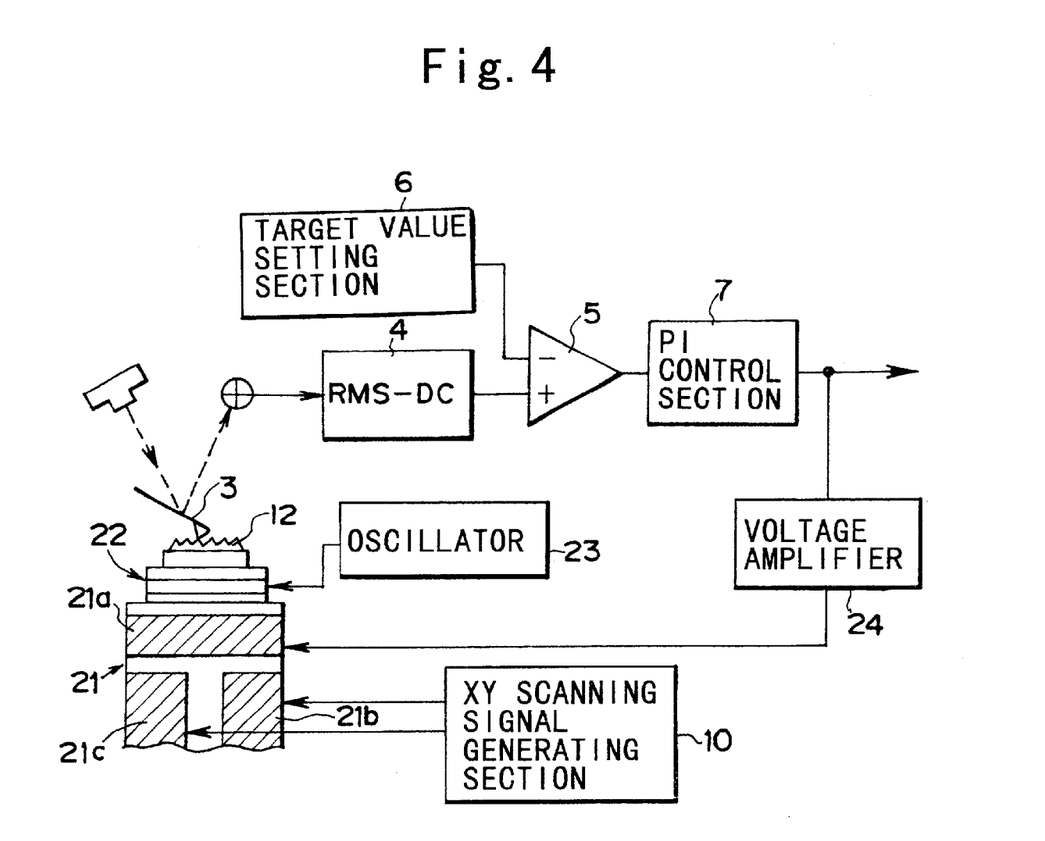
[FIG. 4] A block diagram of a second embodiment of the present invention.

Another embodiment of the present invention will be explained with reference to FIG. 3. In FIG. 4, the same reference character as FIG. 1 denotes the identical or equivalent element. This embodiment is characterized in that a multi-layer piezoelectric element is placed on the piezoelectric scanner to place a sample thereon so that the sample is forcibly vibrated.

In FIG. 4, the cantilever 3 is fixed by a not-shown jig. At a location opposite to the cantilever 3, a sample 12 is placed which is rested on a piezoelectric scanner 21 through a multi-layer piezoelectric element 22. The multi-layer piezoelectric element 22 is, as well known, layered in a same direction with a plurality of piezoelectric plates of a same polarity so that when the multi-layer piezoelectric element 22 is applied by a drive voltage the displacement of each sheet is added together for increase.

Explaining the operation of the present embodiment, the oscillator 23 is first operated to actuate the Z servo system while forcibly vibrating the sample 12. The frequency to forcibly vibrate the sample 12 is set at a frequency that is free of affection of the resonant frequencies inherent to the cantilever 3 and the sample 12, similarly to the case of the former embodiment. When this operation proceeds and the probe needle 3a comes into contact with the sample 12 so that an output signal of the RMS-DC circuit 4 becomes ΔA in FIG. 2, the Z rough movement is ended. Then a scanning signal output of the XY scanning signal generating section 10 is applied to the X, Y direction drive electrodes 21b, 21c of the piezoelectric scanner 1, entering to an actual observation.

In this manner, according to the present embodiment, the sample 12 is raised while being forcibly vibrated at a frequency substantially free of affection of the resonant frequencies inherent to the cantilever 3 and the sample 12, and the Z rough movement is ended at a position where the cantilever 3 becomes a predetermined contact pressure with the sample. Accordingly, it is possible to easily initially set constant at all times the pressure that the needle tip of the cantilever taps the sample surface even if the cantilever is exchanged, similarly to the first embodiment. Also, if the cantilever is exchanged, it becomes possible to obtain stable sample surface detection data without variation at all times.

In also the case of the embodiment shown in FIG. 4, similarly to the case of the embodiment explained before, the forcible vibration frequency of the cantilever 3 can be changed to a structure with a resonant frequency f1 or f2 newly caused by contacting the cantilever 3 with the sample 12 or a structure with a shift resonant frequency fc shown in FIG. 3. Although it is natural that this provides a similar effect, the detail of it has already been concretely explained and repeated explanation is omitted here.

Figure 5:
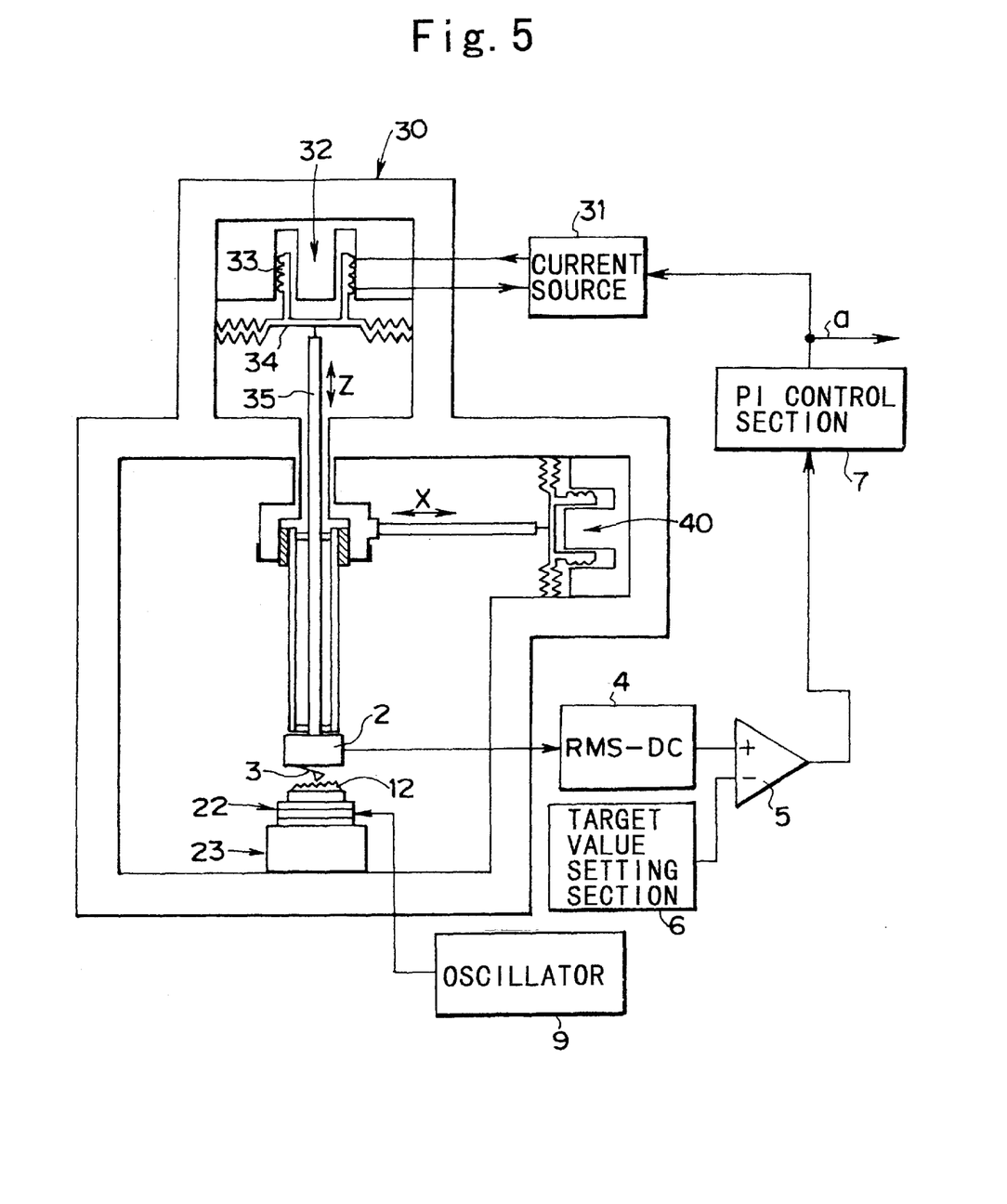
[FIG. 5] A block diagram of a third embodiment of the present invention.

Another embodiment of the present invention will be explained with reference to FIG. 5. In FIG. 5, the same reference character as FIG. 1 denotes the identical or equivalent element. This embodiment is characterized in that the present invention is realized by a scanning probe microscope 30 using a voice coil motor.

As shown in the figure, if a current is passed to a coil 33 of a voice coil motor 32 in the Z direction from a current source 31 in response to an output from the PI control section 7, a mover 34 is driven downward in the figure and the cantilever 3 attached to the optical lever detecting section 2 at an end of a spindle 35 is roughly moved in the Z direction. Accordingly, in the present embodiment the oscillator 9 is operated to effect Z rough movement by actuating the Z servo system while forcibly vibrating the sample 12 by the multilayer piezoelectric element 22. The Z rough movement is ended at a position where the contact pressure of the cantilever 3 against the sample 12 becomes ΔA in FIG. 2. The vibration frequency of the sample 12 at this time is set at a frequency that is substantially free of affection of the resonant frequencies inherent to the cantilever 3 and the sample 12.

Subsequently, XY scanning signals are applied to an X-direction voice coil motor 40 and a not-shown Y-direction voice coil motor. By doing so, it becomes possible to obtain geometry data on the surface of the sample 12 from the optical lever detecting section 2, similarly to the conventional tapping mode. Incidentally, the operation of the scanning probe microscope 30 in the present embodiment is explained in detail in Japanese Patent Application No. H8-118015 filed by the present applicant, and explanation is omitted. The similar effect to the above embodiment can be also obtained by the structure of the present embodiment.

In also the embodiment shown in FIG. 5, the forcible vibration frequency of the sample 12 can be changed to a structure with a resonant frequency f1 or f2 newly caused by contacting the cantilever 3 with the sample 12 or a structure with a shift resonant frequency fc shown in FIG. 3. Although it is natural that this provides a similar effect, the detail of it has already been concretely explained and repeated explanation is omitted here.

Each of the embodiments of the present invention as explained above is one example of the present invention. It is natural that the present invention is never limited to these structures of the embodiments. In brief, such an invention can be considered within the scope of the present invention that includes a method and apparatus to measure, as a gist of the present invention, on a sample by lightly contacting a cantilever therewith while forcibly vibrating the sample by avoiding a resonant frequency of the single cantilever or single sample.

According to the present invention, as stated above, the pressure that a needle tip of the cantilever taps a sample surface can be easily initially set constant at all times even if the cantilever is exchanged. Also, due to this, if the cantilever is exchanged, it becomes possible to stably obtain detection data on the sample surface without variation.

According to a structure that the sample is vibrated at a resonant frequency newly caused upon contacting the cantilever with the sample regardless of free vibration of a single body of the cantilever or sample, the sensitivity of measurement can be enhanced. Besides, because vibrational amplitudes can be determined largely different due to contact or noncontact of the cantilever with the sample, it can be detected extremely accurately whether the cantilever is contacted with the sample or not, helping for performance improvement. Also, because the sample is put in vibration to bring the cantilever into contact with this, the vibrational amplitude of the cantilever tends to increase as the cantilever is approached the sample. Due to this, it is possible to increase detection sensitivity. In this manner, because of a detection method that the vibrational amplitude reaches maximum where the probe needle extremely approaches the sample in a manner different from the tapping mode, the S/N ratio of the detection signal improves and the detection characteristic stabilizes where the probe needle extremely approaches the sample.

In the case where measurement is conducted while vibrating the cantilever at a new resonant frequency that has shifted upon contacting the cantilever with the sample regardless of free vibration of a single body of the cantilever or sample, it is possible to enhance measurement sensitivity and make greatly different the vibrational amplitudes due to contact or noncontact of the cantilever with the sample. Accordingly, it can be accurately detected whether the cantilever is contacted with the sample or not, helping for performance improvement. Furthermore, even where the cantilever possesses two or more resonant frequencies, a required measurement is possible if a resonant frequency caused by coupling between the sample and the probe needle lies intermediate between them.

According to an apparatus of the present invention, because the Z servo system holds equilibrium at a point where the contact pressure of the cantilever against the sample becomes a predetermined magnitude, initial setting for measurement (Z rough movement) is easy to perform. The scanning probe microscope can be easily handled even by one who is not skillful.

What is claimed is:

1. A method of measuring a geometry of a surface of a sample, comprising the steps of:
    providing a sample;
    providing a scanning probe microscope having a cantilever probe;
    vibrating the cantilever probe;
    contacting the vibrating cantilever probe with a surface of the sample;
    measuring a resonant frequency of the cantilever probe while in contact with the surface of the sample; and
    measuring a geometry of the surface of the sample while vibrating the sample at the measured resonant frequency of the cantilever probe.

2. A method according to claim 1; wherein the scanning probe microscope has a Z servo system operating in a given frequency range for controlling rough movement of the cantilever probe in the Z direction; and wherein the measured resonant frequency of the cantilever probe is greater than the operating frequency range of the Z servo system.

3. A method according to claim 2; wherein the contacting step comprises effecting rough movement of the vibrating cantilever probe in the Z direction toward the surface of the sample until the vibrating cantilever probe contacts the surface of the sample and stopping rough movement of the cantilever probe in the Z direction when a contact pressure of the cantilever probe against the sample reaches a given magnitude.

4. A method according to claim 1; wherein the contacting step comprises effecting rough movement of the vibrating cantilever probe in the Z direction toward the surface of the sample until the vibrating cantilever probe contacts the surface of the sample and stopping rough movement of the cantilever probe in the Z direction when a contact pressure of the cantilever probe against the sample reaches a given magnitude.

5. A method according to claim 1; wherein the step of measuring the geometry of the surface of the sample comprises measuring the geometry of the surface of the sample while the cantilever probe does not contact the surface of the sample.

6. A method of measuring a geometry of a surface of a sample, comprising the steps of:
    effecting movement of a cantilever probe in the Z direction to bring the cantilever probe into pressure contact with the surface of the sample while the sample is vertically vibrated;
    measuring a resonant frequency of the cantilever probe while in contact with the surface of the sample; and
    measuring a geometry of the surface of the sample while scanning the cantilever probe over the surface of the sample in the XY plane and while vibrating the sample at the measured resonant frequency of the cantilever probe.

7. A method according to claim 6; wherein the measured resonant frequency is substantially unaffected by resonant frequencies inherent to the cantilever probe and the sample.

8. A method according to claim 6; wherein the step of measuring the geometry of the surface of the sample comprises measuring the geometry of the surface of the sample while the cantilever probe does not contact the surface of the sample.

9. A scanning probe microscope comprising:
    a probe for contacting a sample;
    a cantilever supporting the probe at its tip;
    vibrating means for vibrating the cantilever probe;
    means for effecting movement of the cantilever in the Z direction to bring the vibrating cantilever probe into pressure contact with a surface of the sample;
    measuring means for measuring a resonant frequency of the cantilever probe while in contact with the surface of the sample;
    a vibrator for imparting controlled vertical vibrations to the sample; and
    control means for controlling the vibrator to vibrate the sample at the measured resonant frequency of the cantilever probe.

10. A scanning probe microscope according to claim 9; further comprising scanning means for scanning the cantilever in the XY plane over the surface of the sample while the vibrating cantilever probe contacts the surface of the sample.

11. A scanning probe microscope according to claim 10; further comprising means for measuring the geometry of the surface of the sample in accordance with a signal outputted from the scanning means.

12. A scanning probe microscope according to claim 11; further comprising means for imaging the geometry of the surface of the sample.

13. A scanning probe microscope according to claim 9; wherein the vibrator comprises a multi-layered piezoelectric element.

14. A scanning probe microscope according to claim 9; wherein the control means includes means for controlling the vibrator to vibrate the sample at the measured resonant frequency of the cantilever probe while the cantilever probe does not contact the surface of the sample.

* * * * *